United States Patent [19]
Rhind

[11] Patent Number: 5,354,554
[45] Date of Patent: Oct. 11, 1994

[54] CROSSLINKED ANTIBODIES AND PROCESSES FOR THEIR PREPARATION

[75] Inventor: Stephen K. Rhind, Wooburn, United Kingdom

[73] Assignee: Celltech Limited, Slough, United Kingdom

[21] Appl. No.: 824,867

[22] Filed: Jan. 22, 1992

Related U.S. Application Data

[63] Continuation of Ser. No. 603,698, Nov. 16, 1990, abandoned.

[30] Foreign Application Priority Data

Feb. 10, 1989 [GB] United Kingdom ............. 8903021.7

[51] Int. Cl.$^5$ ................... A61K 39/44; A61K 49/02; C07K 17/02
[52] U.S. Cl. .................. 424/1.49; 424/1.53; 424/9; 424/94.3; 424/178.1; 424/179.1; 530/391.1; 530/391.3; 530/391.5; 530/391.7; 530/391.9; 436/544; 436/545; 436/546; 435/188
[58] Field of Search .............. 530/391.1, 391.3, 391.5, 530/391.7, 391.9, 866; 424/85.8, 85.91, 94.3, 1.1, 9; 435/188, 972; 436/544, 545, 546

[56] References Cited

U.S. PATENT DOCUMENTS

| | | | |
|---|---|---|---|
| 4,671,958 | 6/1987 | Rodwell et al. | 424/85.91 |
| 4,741,900 | 5/1988 | Alvarez et al. | 424/85.91 |
| 4,751,286 | 7/1988 | Packard et al. | 530/388 |
| 4,889,916 | 12/1989 | Packard et al. | 525/54.1 |
| 4,981,979 | 1/1991 | Sivam | 530/390 |
| 5,185,433 | 2/1993 | Dean et al. | 530/391.1 |

FOREIGN PATENT DOCUMENTS

| | | | |
|---|---|---|---|
| 8705030 | 8/1987 | World Int. Prop. O. | C07K 15/00 |
| 8809344 | 12/1988 | World Int. Prop. O. | |
| 8901974 | 3/1989 | World Int. Prop. O. | C12N 15/13 |
| 8911863 | 12/1989 | World Int. Prop. O. | |

OTHER PUBLICATIONS

Blair et al (1983) J. Immunol. Methods 59:129-143.
Franz et al (1987) Nucl. Med. Biol 14(6):569-572.
Moi et al (1988) J. Am. Chem. Soc. 110:6266-6267.
Huston et al (1988) Proc. Natl. Acad. Sci. USA 85:5879-5883.
Bird et al (1988) Science 242:423-426.
Glennie et al (1987) J. Immunol 139:2367-2375.
Staerz et al (1986) Proc. Natl. Acad. Sci USA 83:1453-1457.

*Primary Examiner*—Kay K. Kim
*Attorney, Agent, or Firm*—Mathews, Woodbridge & Collins

[57] ABSTRACT

Cross-linked labelled antibody conjugates are described which have at least one non-disulphide interchain bridge. The bridge may be the residue of a homo- or heterofunctional cross-linking reagent, and is located away from the antigen binding domains of the antibody. The antibody conjugates have an enhanced binding capacity and in vivo have good blood clearance and, in the presence of a tumour high tumour: blood and tumour: bone ratios. The conjugates are of use in the diagnosis and therapy of e.g. tumours and may be prepared by reaction of a cross-linking reagent with an antibody.

19 Claims, No Drawings

CROSSLINKED ANTIBODIES AND PROCESSES FOR THEIR PREPARATION

This is a continuation of application Ser. No. 07/603,698, filed Nov. 16, 1990, now abandoned.

FIELD OF THE INVENTION

This invention relates to cross-linked antibodies, to compositions containing them, to processes for their preparation, and to their use in medicine and for diagnosis.

BACKGROUND TO THE INVENTION

Antibody conjugates, in which antibodies are covalently attached to reporter or effector groups, have been used in diagnosis, and, to a more limited extent, in therapy. The antibody is generally selected on the basis of its affinity and specificity for a particular target antigen, such that, in use, it should be able to deliver the reporter of effector group to a desired site and maintain it there for a length of time.

Bispecific heterodimeric antibodies have been previously described in which Fab' fragments have been joined via a thioether linkage [Glennie M. J. et al J. Immunol. 139, 2367, (1987)]. Antibodies in which the fluorescein derivative crabescein has been linked across a disulphide bond have also been described [Packard, B. P. et al, Biochemistry 25, 3548 (1986)].

We have now found that by cross-linking at least two chains of an antibody in a cross-linkage away from the antigen binding domains the binding capacity of the modified antibody may be advantageously enhanced relative to the unmodified antibody. In vivo, modified antibodies of this type also have good blood clearance and, in the presence of a tumour, give advantageously high tumours; blood and tumour: bone ratios. Such antibodies, when labelled with a reporter or effector group thus offer potential advantages over conventional labelled antibodies.

SUMMARY OF THE INVENTION

Thus, according to one aspect of the invention we provide a cross-linked antibody conjugate comprising a labelled antibody molecule having at least one non-disulphide interchain bridge, said bridge being attached to each chain at one or more bridging sites located outside of the antigen binding domains of the antibody.

In the antibody conjugates according to the invention, the interchain bridge may link any heavy or light chain in the antibody molecule to one or more other heavy and/or light chains in the same molecule. Preferably, however, the bridge will link two chains, particularly two heavy chains. More than one interchain bridge group may be present, although conjugates with one such bridge are preferred.

The term non-disulphide interchain bridge is intended to mean that S-S bridges of the type normally found in antibodies are excluded.

The bridging site in each antibody chain may generally be at the side-chain of an amino acid residue forming part of the chain but not directly participating in the antigen binding domain. Suitable amino acids include those with a side-chain containing an amino, sulphydryl, carboxyl, phenolic or other aromatic or heteroaromatic functional group through which the interchain bridge may be linked. Particular amino acid residues of these types include lysine, cysteine, glutamic acid, aspartic acid and tyrosine residues. Alternatively, the bridging site may be at a carbohydrate residue attached to the antibody chain, particularly an oxidised carbohydrate residue containing at least one aldehyde group through which the interchain bridge may be linked.

Particularly preferred bridging sites are the sulphydryl groups of cysteine residues, for example those normally functioning in interchain disulphide bridges. Preferred sites of this type are sulphydryl groups of cysteine residues present in heavy chains in the hinge region of the antibody.

In another preference, the bridging site may be at the side-chain of an amino acid residue not normally present in the immunoglobulin, but which has been introduced through the use of recombinant DNA techniques as described hereinafter. Such sites include the sulphydryl and amino groups of cysteine and lysine residues respectively.

The interchain bridges in conjugates according to the invention may in general be of any desired length or composition. Suitable bridges include residues of homo- or heterofunctional cross-linking reagents, particularly homo- or heterobifunctional cross-linking reagents. Thus, the bridges may be such that they link two or more bridging sites. Particular bridges include optionally substituted polyvalent, especially bivalent, radicals of aliphatic, aromatic or araliphatic compounds.

The interchain bridge may for example have the structure $[-X^1-]_m-Y^1-Y^2-[-X^2-]_n$ (where $X^1$ and $X^2$ is each the residue of a reactive functional group, $Y^1$ and $Y^2$ together form the remainder of the bridge and m and n, which may be the same or different is each an integer 1 or more).

In bridges of the above particular types $Y^1$ and $Y^2$ together may be straight or branched $C_{1-20}$alkylene (e.g. $C_{1-10}$alkylene such as $C_{4-10}$alkylene, e.g. butylene, pentylene, hexylene, or heptylene), $C_{2-20}$alkenylene or $C_{2-20}$alkynylene chains, optionally interrupted by one or more —O— or —S— atoms or $C_{5-8}$cycloalkylene (e.g. cyclopentylene or cyclohexylene), $C_{6-12}$ aromatic (e.g. phenylene or substituted phenylene), $C_{5-10}$heteroaromatic (e.g. furanyl, pyridyl), —N(R$^1$)— (where R$^1$ is a hydrogen atom or a $C_{1-6}$alkyl group), —CON(R$^1$)— or —N(R$^1$)CO— groups.

In general, residues of reactive functional groups represented by $X^1$ or $X^2$ include residues of any groups capable of reacting with any thiol, amino, carboxyl, hydroxyl, aldehyde, aromatic or heteroaromatic group. Thus, for example, $X^1$ or $X^2$ may be —CH$_2$—, —S—, —NH—, —NHN=, —N(CH$_3$)N=, —NHCONHN=, —NHCSNHN=, —N(Ph)N=(where Ph is phenyl), —NC(O)—, —NC(S)—, —CO—,

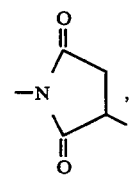

—Het$^1$C(Het$^2$)CH$_2$— (where Het$^1$ and Het$^2$, which may be the same or different, is each a nitrogen containing heterocyclic group, e.g. a pyridyl group, or Het$^1$ is a nitrogen containing heterocyclic group and Het$^2$ is a hydrogen atom), or

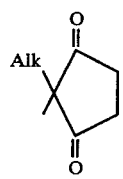

(where Alk is a $C_{1-4}$ alkyl, e.g. methyl group).

It will be appreciated that when the bridge is branched a reactive functional group may be provided in each branch, thus allowing attachment of the bridge to each chain through more than one bridging site.

The term labelled antibody molecule in conjugates according to the invention is intended to mean an antibody molecule to which a reporter or effector group is attached.

Reporter group is to be understood to mean any group or compound which is easily detectable by analytical means in vitro and/or in vivo and which confers this property to the conjugate. Effector group is to be understood to mean any group or compound which is capable of eliciting a change in, or a response from, a biological system and which also confers this property to the conjugates of the invention.

Suitable reporter or effector molecules include radionuclides, e.g. $^{125}I$ and $^{131}I$; chelated metals; fluorescent compounds or compounds which may be detected by NMR or ESR spectroscopy; pharmacological agents, including cytotoxic compounds and toxins, e.g. ricin and fragments thereof; enzymes; and hormones.

Chelated metals include chelates of di- or tripositive metals having a coordination number from 2 up to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and Scandium (Sc). In general the metal is preferably a radionuclide. Particular radionuclides include $^{99m}Tc$, $^{186}Re$, $^{188}Re$, $^{58}Co$, $^{60}Co$, $^{67}Cu$, $^{195}Au$, $^{199}Au$, $^{110}Ag$, $^{111}Ag$, $^{203}Pb$, $^{206}Bi$, $^{207}Bi$, $^{111}In$, $^{67}Ga$, $^{68}Ga$, $^{88}Y$, $^{90}Y$, $^{160}Tb$, $^{153}Gd$ and $^{47}Sc$.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives; and polyamides, especially desferrixoamine and derivatives thereof.

Examples of particular macrocyclic amines include compounds of formula (1)

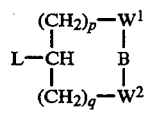

(wherein L is a reactive group, B is a $C_{2-14}$alkylene chain interrupted by one or two optionally substituted nitrogen atoms; $W^1$ and $W^2$, which may be the same or different, is each an optionally substituted nitrogen atom; p is zero or an integer 1 and q is zero or an integer 1 or 2 with the proviso that when p is zero, q is an integer 1 or 2). It will be appreciated that the group L provides an attachment point for the macrocyle in conjugates according to the invention.

Preferred amines of formula (1) include tri-aza derivatives of formula (2):

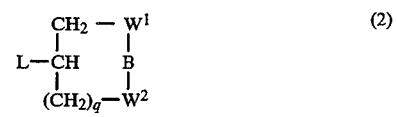

[wherein the group L is as just defined, $W^1$ and $W^2$ which may be the same or different is each a group $-N[(CH_2)_rR^1]-$ (where r is zero or an integer 1 to 6 and $R^1$ is an alkyl, alkoxyalkyl, $-CO_2H$, $-SO_3H$, $-PO_3H_2$ or aryl group) and B is a group $-CH_2(CH_2)_sN(R)(CH_2)_tCH_2-$ (where s and t, which may be the same or different is each zero or an integer 1, 2, or 3; and R represents $-(CH_2)_rR^1$ where r and $R^1$ are as just described)]; and tetra-aza derivatives of formula (3):

[wherein the group L is as just defined, $W^1$ and $W^2$ which may be the same of different is each a group $-N[(CH_2)_rR^1]-$ (as just defined) and B is a group $-CH_2(CH_2)_sN(R)CH_2(CH_2)_dN(R)(CH_2)_tCH_2-$ (where d is zero or an integer 1, 2, or 3 and s, t and R are as just defined].

A particularly useful amine of formula (2) is the compound of formula (4):

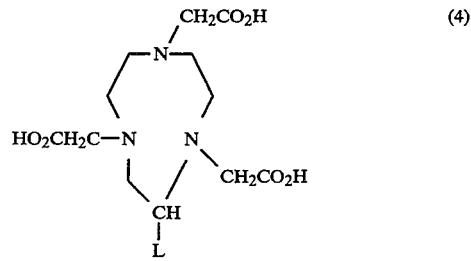

A particularly useful amine of formula (3) is the compound of formula (5):

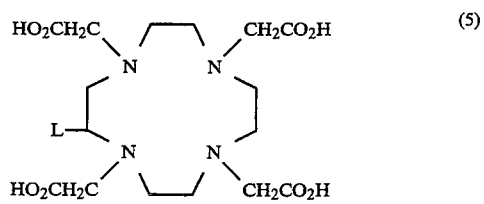

Preferred chelated metals in conjugates according to the invention include indium chelated by a compound of formula (2), particularly the compound of formula (4); or yttrium chelated by a compound of formula (3), particularly the compound of formula (5). $^{111}$In and $^{90}$Y are particularly preferred.

The reporter or effector group may be attached to the antibody either directly (for example as in the case of a radionuclide such as iodine) or indirectly through a reactive functional group, for example a group $X^1$ as described above.

The antibody in the conjugates according to the invention may in general belong to any immunoglobulin class. Thus for example it may be an immunoglobulin M antibody or, in particular, an immunglobulin G antibody, including the isotypes IgG1, IgG2, IgG3 and IgG4. The isotypes IgG1, IgG2 and IgG4 are particularly useful in the conjugates according to the invention, especially the isotypes IgG1 and IgG4.

The antibody molecule may be of animal, for example mammalian origin, and may be for example of murine, rat or human origin. It may be a natural antibody or a fragment thereof, or, if desired, a recombinant antibody or antibody fragment i.e. an antibody molecule or antibody fragment which has been produced using recombinant DNA techniques.

Particular recombiant antibodies or antibody fragments include, (1) those having an antigen binding site at least part of which is derived from a different antibody, for example those in which the hypervariable or complementarity determining regions of one antibody have been grafted into the variable framework regions of a second, different antibody (as described in European Patent Specification No. 239400); (2) recombinant antibodies or fragments wherein non-Fv sequences have been substituted by non-Fv sequences from other, different antibodies (as described in European Patent Specification Nos. 171496, 173494 and 194276); or (3) recombinant antibodies or fragments possessing substantially the structure of a natural immunoglobulin but wherein one or more amino acid residues is or are altered, for example wherein the hinge region of the antibody has a different number of cysteine residues from that found in the natural immunoglobulin, or wherein one or more cysteine residues in a surface pocket of the recombinant antibody or fragment is in the place of another amino acid residue present in the natural immunoglobulin (as described in International Patent Specifications Nos WO89/01974 and WO89/01782 respectively) or wherein a lysine residue is in the place of another amino acid residue present in the natural immunoglobulin.

Where the antibody is an antibody fragment, it may be for example a proteolytic fragment, obtained by enzymatic digestion of a whole antibody. Alternatively, the antibody fragment may be a fragment obtained by recombinant DNA techniques, for example Fv fragments (as described in International Patent Specification No. WO89/02465).

In general, conjugates according to the invention in which the antibody is an antibody fragment, particularly a F(ab')$_2$ fragment are preferred.

The antibody may be polyclonal or, preferably, monoclonal origin. It may be specific for any number of antigenic determinants, but is preferably specific for one. The antigenic determinant may be any hapten or an antigenic determinant associated with any antigen. Particular antigens include those associated with animals, e.g. humans, [for example normal animal tissue or organ cell-associated antigens, tumour cell-associated antigens (for example oncofetal antigens such as carcinoembroyonic antigen or alphafetoprotein, placental antigens such as chorionic gonadotropin and placental alkaline phosphatase, and prostate antigens such as prostatic acid phosphatase and prostate specific antigen) and antigens associated with components of body fluids such as fibrin or platelets], viruses, bacteria and fungi.

In a preferred aspect the antibody may be capable of recognising and binding a tumour cell-associated antigen, particularly one or more epitopes on the TAG-72 antigen associated with human breast and colon tumours. A particularly preferred antibody of this type is the monoclonal antibody B72.3 [Colcher, D. et al Proc. Nat. Acad. Sci. USA (1981), 78, 3199] or a fragment thereof, particularly a F(ab')$_2$ fragment.

One preferred group of conjugates according to the invention is that wherein each antibody conjugate comprises a labelled antibody molecule having a non-disulphide inter-heavy chain bridge, said bridge being attached to each heavy chain through the sulphydryl group of a cysteine residue present in each of said chains in the hinge region of said antibody molecule.

Particularly useful conjugates of this type are those in which the antibody has only one cysteine residue present in each heavy chain in the hinge region, said cysteine residues forming the bridging sites for the interchain bridge.

Other useful conjugates of this type are those wherein the antibody is capable of recognising and binding a tumour cell-associated antigen, especially one or more epitopes on the TAG-72 antigen associated with human breast and colon tumours. The antibody may be a naturally occurring antibody or fragment thereof, particularly a F(ab')$_2$ fragment, or a recombinant antibody or antibody fragment as hereinbefore described. The antibody is preferably a B72.3 antibody or fragment thereof, including a recombinant B72.3 antibody or fragment thereof.

In conjugates of this preferred type the label is preferably an iodine atom, especially $^{125}$I or $^{121}$I, or a chelating agent of formula (1) particularly be a compound of formulae (2) or (3), especially a compound of formulae (4) or (5) complexed with a metal. The metal is preferably a di- or tripositive metal having a coordination number from 2 up to 8 inclusive and is especially a radionuclide. Indium, especially $^{111}$In and yttrium, especially $^{90}$Y are particularly preferred.

The conjugates according to the invention are of use as diagnostic or therapeutic agents. Thus depending on the nature of the antibody and the reporter or effector group, the conjugate may be used in vivo in conjunction with a suitable detector to image normal or diseased tissues, including tumours and thrombi; or in the treatment of abnormal cell disorders, e.g. tumours, thrombi and diseased, including infected, tissues. Alternatively, conjugates according to the invention may be of use in in vitro diagnostic techniques, for example in radioimmunoassays or enzyme-linked immunoassays.

Thus according to a further aspect of the invention we provide an antibody conjugate for use in a method of treatment or diagnosis of a human or animal subject, said antibody conjugate comprising a labelled antibody molecule having at least one interchain bridge, said bridge being attached to each chain at one or more bridging sites located outside of the antigen binding domains of the antibody.

For in vivo use the antibody conjugate may be formulated as a suitable composition in an appropriate dosage.

Thus according to another aspect of the invention there is provided a pharmaceutical composition comprising a labelled antibody molecule having at least one non-disulphide interchain bridge said bridge being attached to each chain at one or more bridging sites located outside of the antigen binding domains of the antibody; together with one or more pharmaceutically acceptable carriers or excipients.

In vivo administration of the conjugate may be by any suitable route, and is preferably parenteral, e.g. by injection or infusion. Suitable formulations of the conjugate for parenteral administration include suspensions, solutions or emulsions of the conjugate in oily or aqueous vehicles, and may contain formulatory agents such as suspending, stabilising and/or dispersing agents. Alternatively, the conjugate may be in powder form for reconstitution with a suitable vehicle, e.g. sterile pyrogen-free water, before use. If desired, the conjugate may be presented in unit dosage form, and/or together with one or more other active ingredients or imaging agents.

The precise doses at which the conjugate will be administered will depend on the route of administration, nature of the antibody and reporter or effector group and the intended use, i.e. whether for diagnosis or therapy, together with other variables such as the body weight and pathology of the patient. Thus the dose for any application will usually need to be determined empirically, using standard procedures.

Where the conjugate according to the invention is intended for in vitro diagnosis it may be adapted for use employing conventional procedures, for example as described in Methods in Enzymology 84, 1982, and 92, 377–523, 1983 (Gen. Ed. Langone, J. J. and Van Vunakis, H, Academic Press, N.Y.).

Conjugates according to the invention may generally be prepared by reaction of an antibody or a fragment thereof whith a cross-linking reagent. It will be appreciated that the cross-linking reaction may be effected with either a labelled or unlabelled antibody molecule.

The reaction may generally be effected in a suitable solvent, e.g. an aqueous solvent such as water or an aqueous inorganic or organic buffer e.g. a phosphate, citrate or acetate buffer or mixtures thereof; or an aqueous organic solvent for example aqueous acetone or dimethylformamide, at any appropriate temperature, for example in the range 0°–30° C., especially around room temperature.

It will be appreciated that in cross-linking reactions of this general type, where the antibody and/or reporter and effector groups when present contain a number of potentially reactive groups, indiscriminate cross-linking can occur, leading to a heterogeneous mixture of products. To avoid this, the general cross-linking method may be adapted, through appropriate choice of reactants and/or reaction conditions either alone or in combination, to obtain a homgeneous product.

Thus, in one option, cross-linking reagents may be chosen with functional groups that selectively react with specific functional groups in the antibody. There are numerous examples of such groups, for example amino-reactive and thiol-reactive functional groups, well-known to the skilled man, [for example as described in European Patent Specifications Nos. 173629 and 175617, UK Patent Specification No. 2109407 and International Patent Specification No. WO 88/05433] which under appropriate conditions react in a selective manner.

In a second option, potentially reactive groups in the antibody and/or reporter or effector group, which it is not desired to cross-link, may be protected before the cross-linking reaction is effected. Conventional procedures for the protection of reactive groups in proteins may be employed, together with standard deprotection techniques.

In a further option, the antibody may be chosen such that it possesses at least one pair of unique bridging sites, which may be utilised for the cross-linkage. Thus, it is possible to partially reduce an antibody, for example using a mild reducing agent such as $\beta$-mercaptoethylamine, such that free sulphydryl groups are generated from the disulphide bridges linking the heavy chains of the antibody, while the remainder of the molecule remains substantially unaffected. The sulphydryl groups may then be used as bridging sites for selective reaction with a thiol specific cross-linking reagent. Alternatively, the antibody may be oxidised, using chemical or enzymatic techniques, e.g. as described in European Patent Specification No. 173629, to generate aldehyde groups in carbohydrate side chains which may then be reacted with a cross-linking reagent as generally described above.

In a further alternative, unique bridging sites may be introduced into an antibody using recombinant DNA techniques, prior to reaction with the cross-linking reagent. Thus, for example, an antibody may be provided wherein the number of cysteine residues in the hinge region of each heavy chain has been reduced to one. This may be conveniently obtained by initially producing in an expression vector an operon which includes a DNA sequence encoding an antibody heavy chain having a hinge region normally associated with the CH1 domain of the antibody molecule.

The operon may be produced by splicing a DNA sequence encoding the CH1 region from an antibody of one class to a DNA sequence encoding the hinge region from an antibody of a different class. Alternatively, it may be produced by cloning the CH1 domain and hinge region from an antibody of one class and altering the number of cysteine residue encoding DNA triplets to one such triplet, by site directed mutagenesis, for example by mutation to alanine-encoding sequences. Transfection of a suitable cell line with the vector and subsequent culturing of the transfected line then produces the desired heavy chain polypeptide.

Since the vector only encodes the heavy chain polypeptide, it will be necessary to arrange for the cell line to produce a complementary light chain. In order to ahieve this, one of three alternative strategies may be employed. Thus, in a first alternative, the cell line may be transfected with a second vector, the second vector encoding a complementary light chain-derived polypeptide. Preferably the vectors are identical except in so far as the coding sequences and selectable markers are concerned, so as to ensure as far as possible that each polypeptide chain is equally expressed.

In a second alternative, the vector may include sequences coding for both light chain and heavy chain-derived polypeptides. In a third alternative, a host cell which naturally secretes a complementary light chain may be used. The general methods by which the vectors may be constructed, transfection methods and culture methods are well known (see for example Maniatis et al, Molecular Cloning, Cold Spring Harbor, N.Y., 1982; Primrose and Old, Principles of Gene Manipulation, Blackwell, Oxford 1980). The above method is more particularly described in International Patent Specification No. WO89/01974.

It will be appreciated that the above-described techniques may be adapted to yield any size heavy chain-light chain pair containing a hinge region with one cysteine residue. Such constructs may be reacted with a cross-linking reagent as generally described above and in the Examples below.

Using similar recombinant DNA techniques to those just described (see also International Patent Specification No. WO89/01782) a cysteine residue may be introduced into each heavy chain of an antibody molecule to provide unique bridging sites for subsequent reaction with a cross-linking reagent to produce a conjugate according to the invention. The methods described may also be used in suitably adapted form with appropriate starting materials where it is desired to produce other recombinant antibodies, for example recombinant antibodies containing additional lysine groups or other amino acids which provide unique bridging sites, for the cross-linking reagent.

Generally, we have found that in cross-linking reactions to produce compounds according to the invention, particularly where the antibody has unique bridging sites, for example as described above, it is preferable to react the cross-linking reagent with excess of antibody. By doing this, indiscriminate cross-linking is avoided and the desired antibody product is produced in good yield, and purity. Cross-linking reactions in which the antibody is used in excess concentration (for example 2× and greater excess) relative to the cross-linking reagent form a further feature of the invention.

Where in the conjugates of the invention the reporter or effector group is a chelated metal, the last step in the preparation of the conjugate may be a reaction to introduce the metal. The metal may be introduced by reacting an antibody with a metal salt (for example a metal halide) in an appropriate solvent, for example an aqueous or non aqueous solvent, (e.g. acetonitrile, acetone, propylene carbonate, dimethylformamaide or dimethylsulphoxide) at any suitable temperature from 0° C. to 50° C., e.g. around room temperature.

Antibodies for use as starting materials in the preparation of conjugates according to the invention may be obtained by conventional means, for example from the sera of immunised animals, or preferably, myeloma or hybridoma cells, or by recombinant DNA techniques as described in European Patent Specifications 171496, 173494, 194276 and 239400 and International Patent Specifications Nos. WO89/01974, WO89/01782, WO89/02465 and WO89/01783. Antibody fragments may be prepared from whole antibodies by enzymatic or chemical means or a combination of both in accordance with conventional practice, or by the aforementioned recombinant DNA techniques suitably adapted to produce a fragment in place of a whole antibody.

Cross-linking reagents for the preparation of conjugates according to the invention may in general be a heterofunctional cross-linking reagent. Methods for obtaining heterofunctional cross-linking reagents are well-known [see for example Ghose, T. I. et al in Methods in Enzymology (1983), 93, 280–333].

Effector or reporter groups for use in the conjugates according to the invention are readily available, (for example see UK Patent Specification 2109407, US Patent Specification 4472509, European Patent Specification No. 175617 and International Patent Specifications Nos. WO89/01475 and WO89/01476) or may be obtained from these known compounds by simple chemical modification using conventional techniques, or may be prepared from known starting materials using methods analogous to those used for the preparation of the known compounds.

Particular macrocyclic amines of formulae (1) (2) and (3) may be prepared by the methods described in International Patent Specifications Nos. WO89/01475 and WO89/01476.

Reporter of effector groups may be linked to the antibody using conventional means. Thus, for example, iodine may be directly linked to the antibody using the chloramine T method (see for example US Patent Specification 4331647), while other reporter or effector groups may be linked by reaction of suitable functional groups on the reporter or effector group with the antibody using standard procedures, for example as described in UK Patent Specification No. 2109407 and International Patent Specifications Nos. WO89/01475 and WO89/01476.

DESCRIPTION OF SPECIFIC EMBODIMENTS

The following Examples illustrate the invention.

EXAMPLE 1

(a) Preparation of F(ab')$_2$ fragments from B72.3 IgG [Colcher, D et al Proc. Nat. Acad. Sci. USA (1981), 78, 3199]. F(ab')$_2$ fragments were prepared from B72.3 IgG by digestion with bromelain. The bromelain was first activated by incubating a 1.0 mg/ml solution with 50 mM cysteine in 0.1M acetate pH 5.50, containing 3 mM EDTA at 37° C. for 30 minutes. Activated bromelain was deslated into 0.1M acetate pH 5.50, containing 3 mM EDTA, using a PD10(Sephadex G25) column, to remove cysteine and added to a 2/0 mg.ml solution of B72.3 (1(w.w):50(w/w) enzyme:IgG) in the same buffer. The digest was incubated at 37° C. for about 2 hours and conversion from Ig G to a F(ab')$_2$ sized peak monitored by SDS-PAGE. After competion of the digestion, antipain and leupeptin were added (final concentration 0.05 mg/ml) and the pH of the mixture adjusted to pH 6.0 with NaOH for subsequent S Sepharose Fast Flow ion-exchange chromatography. The F(ab')$_2$, Fc and remaining IgG eluted in the flow through and the bromelain remained bound to the matrix. This negative purification step effectively removed all the bromelain from the digest mixture.

(b) Purification of F(ab')$_2$ fragements.

The remaining digest mixture was first dialysed into 20 mM Tris pH7.8 and loaded onto a DEAE Sepharose Fast Flow column. The F(ab')$_2$ eluted from the column in the flow through whilst the Fc portion and remaining intact IgG were retained. The bound material was eluted from the matrix with 0.1M NaCl in 20 mM Tris pH7.8 to regenerate the column.

(c) Preparation of chemically cross-linked F(ab')$_2$ molecules.

B72.3 F(ab')$_2$ at 5.0 mg/ml in 0.15M phosphate buffer pH8.0, containing 2 mM EDTA was reduced by the addition of 2-mercraptoethylamine to a final concentration of 5 mM and incubation at 37° C. for 30 minutes. After reduction, the sample was desalted down a Sephadex G25 (Pharmacia) column equilibrated with 0.1M citric acid/0.2M Na$_2$HPO$_4$ pH6.0 containing 2 mM EDTA.

1,6-Bismaleimidohexane was dissolved in dimethylformamide to a final concentration of 72 mM and added to the feshly reduced Fab'SH at a level of 0.9 mM (approximately 22 fold excess over titratable thiols). After 90 minutes incubation with constant mixing at room temperature N-ethyl maleimide was added to a final concentration of 9 mM and incubated further for 30 minutes before desalting into 0.1M citric acid/0.2M Na2HPO4 2 mM EDTA. The maleimidated Fab' (Fab'-mal) was immediately added to a fresh batch of Fab'SH at a molar ratio of Fab'mal:Fab'SH of 1.1:1.0 and incubated at room temperature with constant mixing for about 20 hours. The cross-linked F(ab')2 was purified from the reaction mixture by HPLC gel filtration.

The composition of the cross-linking reaction mixture was determined by HPLC gel filtration after the overnight incubation. 10 μl of the reaction mixture was added to 10 μl of 200 mM 2-mercaptoethylamine and incubated for 15 minutes. A further addition of 20 μl of 800 mM iodoacetamide was made and reacted for 15 minutes. The reduced and alkylated sample was then analysed by HPLC GF 250 and the percentage composition of the chromatogram determined by integration. The chemically cross-linked molecule eluted with a retention time of 8.62 min whereas unreacted Fab' eluted later at 9.48 min under standard HPLC conditions of 1 ml/min flow rate in 0.2M phosphate buffer pH7.0 mobile phase. The cross-linked F(ab')2 was also verified after purification by reducing SDS-PAGE where the F(ab')2 showed a cross-linked H'-H' band (Mr:~46,000) and L band (Mr~22,000) whereas a control showed the usual H'(Mr:23,000) and L bands (Mr:22,000).

The reaction was repeated using the following cross-linking reagents in place of 1,6-bismaleimidohexane: N,N'-O-phenylene dimaleimide; bismaleimido methyl ether; and lysine bismaleimide.

Each of the cross-linked antibodies prepared above was iodinated using the chloramine T method to yield a conjugate antibody of the invention wherein the label is iodine and the bridging group is either the residue of 1, 6 bismaleimidohexane, N, N¹-O-phenylene dimaleimide, bismaleimide methyl ether or lysine bismaleimide linked to each heavy chain of the antibody through a cysteine bridging site present in the hinge region.

EXAMPLE 2

This illustrates the preparation of chimeric B72.3 Fab' delta cys cross-linked with either 1,6-bismaleimidohexane or lysine bismaleimide. The chimeric B72.3 Fab' delta cys starting material was prepared according to the methods specifically described in International Patent Specifications WO89/01974 and WO89/01783.

Chimeric B72.3 Fab' delta cys at 1.0 to 2.0 mg/ml in 0.1M sodium acetate buffer pH6.0, containing 0.86 mM citric acid and 2 mM EDTA was reduced by the addition of 2-mercaptoethylamine to a final concentration of 5 mM and incubated at 37° C. for 30 minutes. After reduction, samples were desalted down a Sephadex G25 (Pharmacia) column, equilibrated with 0.1M sodium acetate/citrate buffer, pH6.0 containing 2 mM EDTA.

Lysine bismaleimide was dissolved in water and added to the freshly reduced Fab'SH at a concentration of 3.8 mM (approximately 40 fold excess over titratable thiols) and incubated at room temperature for 60 minutes with constant mixing. N-ethyl aleimide was added to a final concentration of 9 mM and incubated further for 30 minutes before desalting into phosphate buffered saline pH7.5. The malemidated Fab' (Fab'mal) was immediately added to a fresh batch of Fab'SH at a weight ratio of Fab'mal:Fab'SH of 1.1:1,0 and incubated at room temperature with constant mixing for about 20 hours.

The composition of the cross linking reaction mixture was determined by HPLC gel filtration after the overnight incubation. 10 μl of the reaction mixture was added to 10 μl of 200 mM 2-mercaptoethylamine and incubated for 15 minutes. A further addition of 20 μl of 800 mM iodoacetamide was made and reacted for 15 minutes. The reduced alkylated sample was then analysed using HPLC (Zorbax GF-250 gel filtration column) and the percentage composition of the chromatogram determined by integration. Material cross-linked with lysine bismaleimide eluted with a retention time of 8.62 min whereas unreacted cFab' eluted later at 9.48 min under standard HPLC conditions of 1 ml/min flow rate in 0.2M phosphate buffer pH7.0 mobile phase. The cross-linked material was also verified after purification by reducing SDS-PAGE where it showed a cross-linked H'-H' band (Mr:~46,000) and L band (Mr:~22,000) whereas a control showed the usual Hl (MR;23,000) and L bands (Mr:22,000).

The experiment was repeated using 1,6-bismaleimidohexane in dry dimethylformamide in place of the lysine bismaleimide in water to yield antibody material cross-linked with bismaleimidohexane.

The products from both experiments were iodinated using the chloramine T method to yield a conjugate antibody of the invention wherein the label is iodoine and the bridging group is either the residue of lysine bismaleimide or 1,6 bismaleimidohexane, linked to each heavy chain of the antibody through the single cysteine residue present in each chain.

EXAMPLE 3

The experiments described in Example 2 were repeated except that each cross-linker was added to the reduced Fab'SH at a molar equivalent ratio of Fab'SH:cross-linker of 2.2:1. After incubation at 37° C. for 60 minutes, cross-linked material was isolated as described in Example 2 and shown by SDS-PAGE to be identical to the material obtained in Example 2. Subsequent iodination as described in Example 2 yield labelled cross-linked antibody.

I claim:

1. A labelled antibody fragment conjugate comprising
   (a) an antibody fragment specific for one antigenic determinant,
   (b) at least one non-disulphide interchain bridge cross-linking said antibody fragment, said bridge being attached to each chain at one or more bridging sites located outside of the antigen binding domains of the antibody fragment, the bridging site comprising an amino, sulphydryl, carboxyl or phenolic group present in the side-chain of an amino acid residue or an oxidized carbohydrate residue attached to the antibody chain, and
   (c) a reporter or effector group covalently bound to said antibody fragment independently of said non-disulphide interchain.

2. The labelled antibody fragment conjugate according to claim 1 wherein said bridging site is a sulphydryl group present in the side-chain of a cysteine residue.

3. The labelled antibody fragment conjugate according to claim 2 wherein the sulphydryl bridging sites are cysteine residues present in each heavy chain in the hinge region.

4. The labelled antibody fragment conjugate according to claim 3 wherein the cysteine residue is the only cysteine residue present in the hinge region.

5. The labelled antibody fragment conjugate according to claim 1 wherein the antibody fragment is a recombinantly produced antibody fragment.

6. The labelled antibody fragment conjugate according to claim 1 wherein the antibody fragment is a F(ab')$_2$ fragment.

7. The labelled antibody fragment conjugate according to claim 1 wherein the interchain bridge has the structure —$X^1$—$Y^1$—$Y^2$—$X^2$— wherein each of $X^1$ and $X^2$ is the residue of a reactive functional group, and $Y^1$ and $Y^2$ together form the remainder of the bridge.

8. The labelled antibody fragment conjugate according to claim 7 wherein each of $X^1$ and $X^2$ is a sulphydryl-reactive group and —$Y^1Y^2$— is a straight or branched alkylene, alkenylene, or alkynylene chain of up to 20 carbon atoms, optionally interrupted with —O— or —S—.

9. The labelled antibody fragment conjugate according to claim 1 wherein the reporter or effector group is a radionuclide, a chelated metal, a fluorescent compound, a compound which can be detected by NMR or ESR spectroscopy, a pharmacological agent, and enzyme or a hormone.

10. The labelled antibody fragment conjugate according to claim 1 wherein the reporter or effector group is a radionuclide or chelated metal.

11. The labelled antibody fragment conjugate according to claim 10 wherein the radionuclide is radioiodide.

12. The labelled antibody fragment conjugate according to claim 1 wherein the reporter or effector group is a chelate of a di- or tripositive metal having a coordination number from 2 up to 8 inclusive and a polydentate chelating agent.

13. The labelled antibody fragment conjugate according to claim 1 wherein the reporter or effector group is an acyclic or cyclic polyamine.

14. The labelled antibody conjugate according to claim 13 wherein the reporter or effector group is a chelate of a di- or tripositive metal having a coordination number from 2 up to 8 inclusive and a cyclic polyaminocarboxylic acid chelating agent.

15. The labelled antibody conjugate according to claim 14 wherein the cyclic polyaminocarboxylic acid is a 1,4,7-triazacyclononane-N, N', N''-triacetic acid.

16. The labelled antibody conjugate according to claim 14 wherein the cyclic polyaminocarboxylic acid is 1,4,7,10-tetraazacyclododecane-N, N', N'', N'''-tetraacetic acid.

17. The labelled antibody fragment conjugate according to claim 13 wherein the acyclic polyamine is a polyaminocarboxylic acid.

18. The labelled antibody fragment conjugate according to claim 13 wherein the cyclic polyamine is a tri-aza or tetra-aza cyclic polyamine.

19. A pharmaceutical composition comprising a labelled antibody fragment conjugate according to claim 1 and a pharmaceutically acceptable carrier or excipient.

* * * * *